(12) United States Patent
Alt

(10) Patent No.: US 6,716,237 B1
(45) Date of Patent: Apr. 6, 2004

(54) INTERVENTIONAL SHIELDED STENT DELIVERY SYSTEM AND METHOD

(75) Inventor: Eckhard Alt, Ottobrunn (DE)

(73) Assignee: Inflow Dynamics, Inc., Arlington, VA (US)

( * ) Notice: Subject to any disclaimer, the term of this patent is extended or adjusted under 35 U.S.C. 154(b) by 0 days.

(21) Appl. No.: 09/663,897

(22) Filed: Sep. 18, 2000

(51) Int. Cl.[7] .................................................. A61F 2/06
(52) U.S. Cl. ...................................... 623/1.11; 606/108
(58) Field of Search ..................... 623/1.11; 606/108, 606/191, 192, 194, 195, 198, 200; 604/19, 27, 28, 506–510, 93.01, 96.01, 97.01, 101.01, 101.05, 103.01, 103.14, 264, 523, 528, 532; 600/433–435, 466–470, 585

(56) References Cited

U.S. PATENT DOCUMENTS

| | | | | |
|---|---|---|---|---|
| 4,723,549 A | * | 2/1988 | Wholey et al. | 604/913 |
| 5,320,604 A | * | 6/1994 | Walker et al. | 604/101.03 |
| 5,876,743 A | * | 3/1999 | Ibsen et al. | 424/426 |
| 5,910,154 A | * | 6/1999 | Tsugita et al. | 606/200 |
| 6,022,336 A | * | 2/2000 | Zadno-Azizi et al. | 604/101.05 |
| 6,142,973 A | * | 11/2000 | Carleton et al. | 604/915 |
| 6,290,710 B1 | * | 9/2001 | Cryer et al. | 606/200 |

* cited by examiner

Primary Examiner—David J. Isabella
Assistant Examiner—Urmi Chattopadhyay
(74) Attorney, Agent, or Firm—Crompton, Seager & Tufte LLC

(57) ABSTRACT

A catheter having a distal end for insertion into a lumen of a patient's body includes a deployable semi-permeable membrane for trapping debris dislodged by a stent while allowing perfusion of body fluid through the membrane, mounted distally on said catheter; a stent mounted proximally of the membrane on the catheter; and a deployment system on the catheter for deploying the membrane in advance of deploying the stent. The deployment system is common to both the membrane and the stent. It includes a respective deployment balloon for each of the membrane and the stent. Deployment of the membrane in advance of the stent is controlled by differences in pressure-diameter characteristics of the respective deployment balloons. The deployable semi-permeable membrane is a selectively controllable collapsible mechanism.

13 Claims, 3 Drawing Sheets

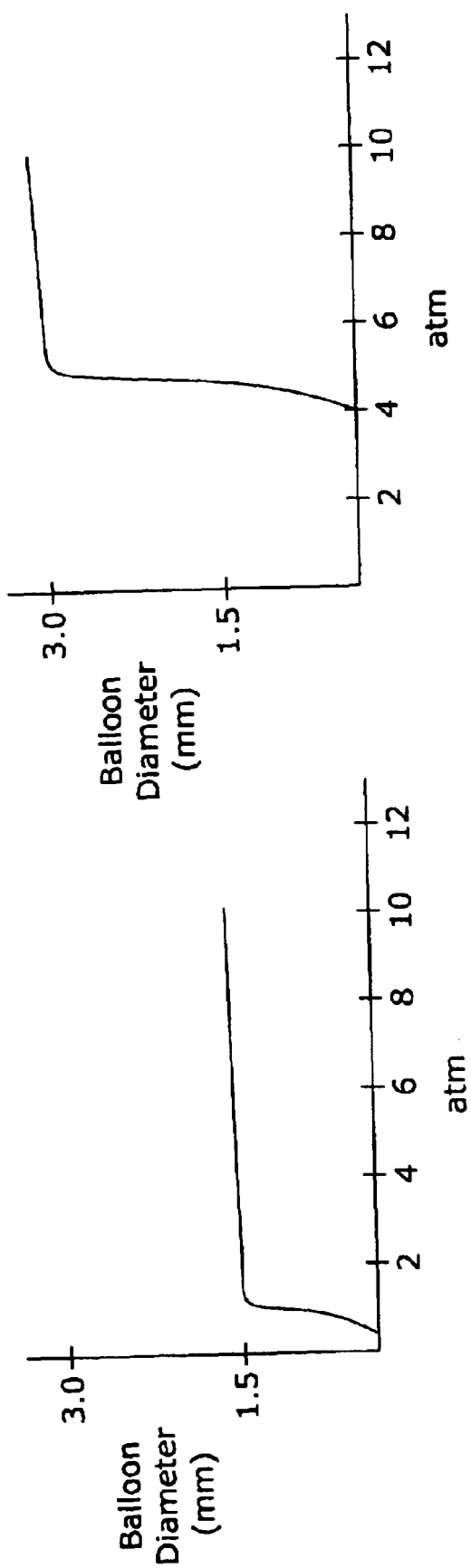

INTERVENTIONAL SHIELDED STENT DELIVERY SYSTEM AND METHOD

CROSS-REFERENCE TO RELATED APPLICATIONS

This application is related to patent application Ser. No. 09/523,763, filed Mar. 11, 2000 ("the '763 application"), of the same inventor and assignee.

BACKGROUND OF THE INVENTION

Interventions in the vascular bed have been increasing dramatically within the past few years. Not only are coronary interventions done with sophisticated tools, higher success rates and new indications, but also interventions in other vessels are performed with increasing success and broadening indications.

Time, speed, cost, precision, accuracy, and final outcome are the major determinants of any progress in the catheterization laboratory. While it has been customary for many years to introduce a guide wire into the lumen and to advance over that guide wire an instrument such as a balloon catheter to work at the specific site, then exchange this balloon catheter for a second one, and finally for therapeutic instruments such as stent delivery catheter, the complexity of such a procedure prohibits very short procedural time for the operation or intervention. In addition, increased amounts of contrast dye are required to localize each of the individual instruments. The use of contrast dye has negative effects on the renal function, on the myocardial function, and on the cerebral function in those patient treated in a catheterization laboratory.

Clearly, it is beneficial for both parties, the medical team and the patient, to reduce the interventional time and systems needed to a minimum.

Clinical evidence has shown that excellent long term results can be obtained with primary stenting. It is understood that with primary stenting no pre-dilatation of a coronary stenosis occurs, since the delivery system which includes a balloon mounted stent is suitable to pass through even a tight lesion.

A problem encountered with stenting is associated with the embolization of debris resulting from the target lesion site which undergoes a considerable change in physical characteristics. The arteriosclerotic masses which cause stenosis in the vessel, such as a coronary, renal, peripheral or carotid stenosis, can be somewhat manipulated when means such as stenting are applied to increasing vessel lumen size. For example, a stenosis which only has a diameter of 0.3 mm is dilated to a diameter of 3.5 mm. Part of this stenosis is squeezed into the vessel wall, but part of this arteriosclerotic build-up, consisting of cholesterol crystals, fibrous tissue, collagen matrix, degenerated inflammatory cells and even most extreme calcifications, are not only displaced into the wall but are also partly embolized to a distal site. At the distal site the emboli cause a perfusion defect, which is in the case of a cardiac intervention a myocardial ischemia and myocardial necrosis, finally resulting in small areas of infarcted myocardium. In case of a carotid operation it is a cerebral perfusion defect which might be transitory, which also might result in a major stroke by blocking important cerebral perfusion downstream following an intervention.

Normally a tight fibrous cap protects the vessel from embolization of this material. With the application of pressure by a balloon, the fibrous cap ruptures, and part of the debris embolizes to a distal site, according to where the blood flows. In the case of the coronary anatomy this is toward the downstream of the myocardium. In the case of a renal artery, this is the renal parenchyma, and in the case of a peripheral artery, this is the peripheral muscles. While embolization in the peripheral muscles can be more easily compensated for at a local site, an embolization, from a carotid artery in the brain for example, has major consequences for the patient, including stroke and disability. Newer methods, such as the utilization of a stent in the affected area, are not really helpful to prevent this type of embolization.

It is a primary aim of the present invention to provide an improved interventional device which enables rapid and effective treatment of a stenosis in a body vessel, and confines the distal embolization of debris from an intervention to a collection area where it is readily removable from the patient's body.

Another aim of the invention to provide an automatic sequential deployment of debris collection means and stenting means so that by the time the stent is deployed, a debris trap has sprung to assure that little or no debris will be allowed to embolize downstream of the intervention.

Yet another aim is to provide a method for operating a balloon catheter stent delivery system in such a way that a debris collection device is automatically deployed immediately prior to deployment of the stent to prevent an escape of debris that would otherwise embolize downstream of the delivery system during an intervention.

SUMMARY OF THE INVENTION

The present invention aims to improve both the challenge of an easier application of an interventional device at the target lesion site with a higher primary success rate despite a tight stenosis, and to effect deployment of a shielding device that protects the downstream perfusion from embolization, and to operatively combine these two devices in order to make an intervention faster, more precise, with fewer side effects and lower cost.

According to the invention, an interventional device for alleviating a stenosed condition in a body lumen includes a catheter; a fixed guide wire located distally on and integral with the catheter; a stent delivery system with a stent located proximally of the fixed guide wire; and a device mounted on the guide wire for collecting debris dislodged by the stent during alleviation of the stenosed condition. The debris collecting device is arranged and adapted to be deployed automatically in advance of deployment of the stent during the same operation of the interventional device that results in deployment of the stent. The debris collecting device includes a porous material mounted in a collapsible mechanism on the fixed guide wire, a first balloon for opening the collapsible mechanism upon inflation and for closing the collapsible mechanism upon deflation. The stent delivery system includes a second balloon on which the stent is mounted for deployment upon inflation and for removal from the delivery system upon deflation. A common pressurization system is provided for inflating and deflating the first and second balloons. The first and second balloons are selected to have different pressurization-diameter characteristics to enable the automatic deployment of the debris collecting device in advance of deployment of the stent.

BRIEF DESCRIPTION OF THE DRAWINGS

The above and still further aims, objectives, features, aspects and attendant advantages of the present invention will become apparent from the following detailed description of a preferred embodiment of the interventional device and method of use thereof, constituting the best mode presently contemplated of practicing the invention, when taken in conjunction with the accompanying drawings, in which:

FIGS. 3A and 3B are charts of the pressure-diameter characteristics of a pair of balloons used in different parts, but related devices, of the overall interventional device of FIGS. 1 and 2.

BRIEF DESCRIPTION OF THE BEST MODE OF PRACTICING THE INVENTION

Figure 1:
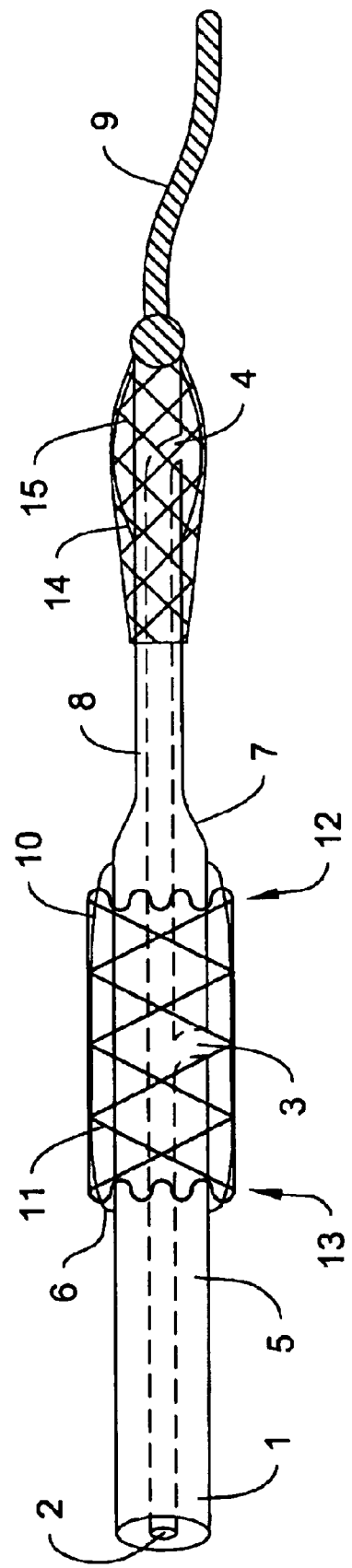
FIG. 1 is a side view of a preferred embodiment of the interventional device of the invention.

FIG. 1 illustrates an interventional device in the form of a modified stent delivery system comprising a balloon catheter 1 and an inner lumen 2. For the sake of convenience and clarity of the description and understanding of the invention, the delivery system as shown in the Figures is not drawn to scale. For example, the proximal portion 5 of catheter 1 would, in practice, generally greatly exceed the length shown in the Figures. The inner lumen 2 runs from the proximal end of catheter 1 to a first opening 3 constituting a rather medially disposed exit orifice of the catheter within a first balloon 6 on which a stent 11 is mounted, and also to a second opening 4 constituting a more distally disposed exit orifice within a second balloon 14 on which an umbrella-like collector device 15 is mounted. The proximal portion 5 of the catheter 1 extends to the balloon 6 of catheter 1 for delivery of the stent 11 mounted thereon to the site of a lesion or other target in the lumen of a vessel, channel, duct or tract (not shown in FIG. 1) of the body of a patient when the interventional device is being used for its intended purpose.

Distal from the balloon 6, the catheter 1 is tapered slightly from a location 7 and through a smooth transition to a thin guide wire 8 of 0.014 inch diameter, for example, which is integral with the catheter. The lumen 2 extends through guide wire portion 8, albeit with smaller diameter than through the proximal part 5 of the catheter, to the second opening 4. The terminal end 9 of the guide wire portion 8 has greater radiopacity than the rest of the catheter 1, by application of a radiopaque surface coating or other conventional means, to allow it to be viewed by x-ray fluoroscopy during insertion of the catheter into a body vessel. Also, this terminal or distal portion 9 is bendable to allow it to more easily navigate a curved or even tortuous path through the vessel lumen as the catheter is being manipulated into place by the attending physician. The guide wire portion 8 of the catheter, encompassing the balloon 14 and umbrella-like collector device 15 corresponds closely to the protective guide wire of the aforementioned co-pending '763 application, and incorporates all of the features thereof herein by reference.

The guide wire is fixed to and integral with the distal end of the stent delivery system to facilitate advancement and exact placement of the stent in a vascular stenosis for deployment at that target site. Preferably, the guide wire has a length of at least 3 centimeters and not more than 20 centimeters. In essence, the guide wire carries an additional protective device to prevent embolization distally of its location resulting from deployment of the stent in a vascular stenosis.

The membrane 10 of balloon 6 is made tightly adherent, along its periphery of attachment, to the body of catheter 1. The stent 11 is mounted tightly or firmly between its distal end 12 and its proximal end 13 over balloon 6, in a reduced-diameter compressed state with a high degree of friction so as to inhibit its movement relative to the balloon membrane 10 when the balloon catheter 1 is advanced through a vessel. Similarly, the membrane of distal balloon 14 is tightly adherent along its periphery of attachment to the guide wire portion 8 of catheter 1.

Thus, it will be understood that the interventional device of the present invention comprises two distinct but related devices on a single catheter body, each of these related devices including its own balloon which is inflatable via the same lumen 2 of the catheter through respective openings 3 and 4 into the interior chamber of the balloon. One device is for delivery and deployment of a stent to a target site in a body vessel, and the other device is for delivery and deployment of an umbrella-operable collection canopy to be positioned downstream of the stent in the body vessel.

Figure 2:
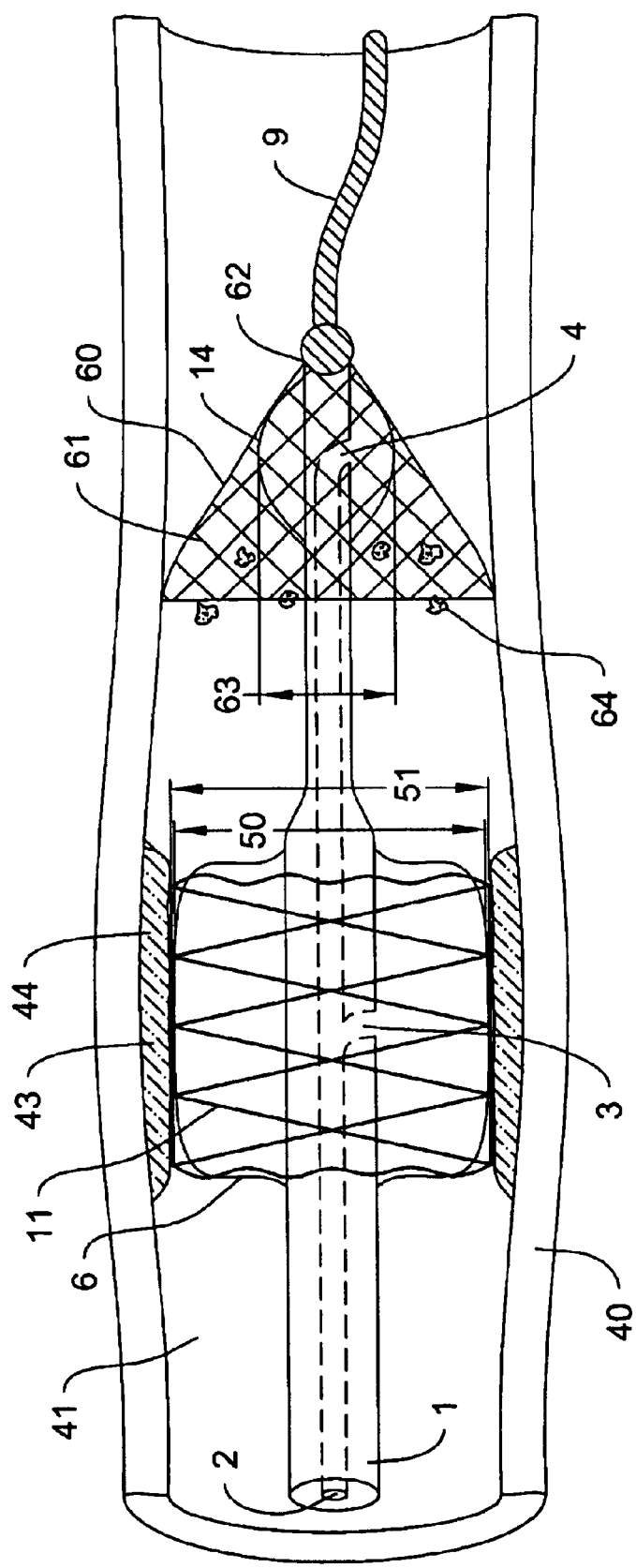
FIG. 2 is a side view of the embodiment of FIG. 1 illustrating the operation of the device in a body vessel shown in fragmentary section view.

Referring now to FIG. 2, the catheter 1 of the interventional device is inserted into the lumen 41 of a vessel of the patient's body, such as an artery 40. The catheter is advanced into the artery lumen until the balloon-mounted stent is positioned adjacent a preselected target lesion site 43 as observed on the fluoroscope. Upon inflation of the balloon 6 via pressurizing channel 2 with saline or saline contrast dye solution through port 3, the balloon is inflated to a larger diameter 50, and the stent 11 is consequently subjected to an outwardly directed radial pressure resulting in its being opened by the inflated balloon to a correspondingly larger diameter 51. The deployed stent is opened to a diameter such that at the target lesion site 43, the arteriosclerotic masses are partly compressed along the length of the stent, and the arteriosclerotic material is squeezed into the vessel wall along site 44. The deployed stent is opened to a diameter such that at the target lesion site 43, the arteriosclerotic masses are partly compressed along the length of the stent, and the arteriosclerotic material is squeezed into the vessel wall along site 42.

At about but not quite the same time (as discussed below), the inflation channel 2 also pressurizes balloon 14 to a larger diameter 63 than its uninflated diameter, but considerably smaller than the diameter 50 of inflated balloon 6. As described in the aforementioned '763 application, umbrella struts 60 are opened from a pivotal attachment 62 located close to the inflating balloon, to correspondingly open a collapsible canopy comprising semi-permeable membrane 61 fastened lineally along the spaced apart struts 60. The balloon 14 is inflated to a diameter sufficient to open the semi-permeable membrane canopy to a new diameter which fully covers the inner lumen 41 of the vessel 40. Yet, the diameter of balloon 14 by which this objective is accomplished is substantially smaller than the diameter of the vessel lumen 41. Accordingly, inflated balloon 14 does not itself significantly block the flow of blood through the lumen via semi-permeable membrane 61.

Thus, the open-canopy of semi-permeable membrane 61 allows the blood cells to perfuse distally through its pores which range from 50 to 150 microns, for example. But the range of sizes of these pores is sufficient to prevent any substantial quantity of debris 64 which results from embolization of a portion of the arteriosclerotic mass 44 when the stent 11 is squeezed against the artery wall at the lesion site 43, from passing distally through the membrane 61. In essence, the opened umbrella canopy acts as a shielding device, in which the debris 64 is collected. In another, but less favorable means of application, the balloon 14 may be dimensioned to operate alone to block the vessel without operating an umbrella to block blood flow and debris embolization.

The pressure-diameter characteristics of the two balloons are intentionally selected to be different, and specifically in a way that will govern the sequence of expansion of the two balloons 14 and 6 to their respective final diameters 63 and 50. The differences between the pressure-diameter characteristics of the two balloons are illustrated in the graphs of FIGS. 3A and 3B.

The pressure-diameter characteristics of the distal umbrella balloon 14 are shown in FIG. 3A. It will be observed that this distal balloon begins to open at a pressure less than one atmosphere and expands to its desired fully inflated diameter of 1.5 mm. at about one atmosphere. This is sufficient to open the umbrella 15 canopy to a diameter equal to the full diameter of the vessel lumen 41. The pressure-diameter characteristics of the more proximal or medial stent balloon 6 are shown in FIG. 3B. In contrast to the opening of the umbrella balloon 14, the stent balloon 6 does not begin to open until the pressure exerted by the saline inflation medium passing through lumen 2 reaches about 4 atmospheres. A pressure of about 5.0 atmospheres is sufficient to expand the stent balloon, and the stent 11 itself, to the full diameter of the vessel and slightly beyond, such as from 3.0 to 3.5 mm.

In practice, this means that after the instrument has been advanced to the target lesion site, the shielding device opens first during the inflation phase. Then, while the shielding device is open to the full diameter of the vessel lumen, the continuing inflation pressurization also opens up the proximal operative stent device, which causes embolization but the resulting debris becomes trapped by the already opened shielding device. When the inflation fluid is exhausted from the balloons via the inflation lumen 2 to allow withdrawal of the interventional device catheter 1, the stent balloon 6 collapses, leaving the stent 11 deployed against the inner surface of the wall of vessel 40, and the umbrella balloon 14 collapses, allowing the umbrella canopy 15 to close and thereby trap the collected debris 64 within its confines. When the catheter is withdrawn, the trapped debris is removed from the patient's body.

Although a preferred embodiment of the invention has been described herein, it will be apparent to those skilled in the art from a consideration of the foregoing disclosure, that variations and modifications of the described embodiment may be made without departing from the true spirit and scope of the invention. Accordingly, it is intended that the invention shall be limited only to the extent required by the appended claims and the rules and principles of applicable law.

What is claimed is:

1. A catheter having a distal end for insertion into a lumen of a patient's body, said catheter comprising:
 a deployable filter membrane for trapping debris while allowing perfusion of body fluid through the membrane, said filter membrane being mounted distally on said catheter;
 a stent mounted proximally of said membrane on said catheter;
 a deployment system for automatically deploying said membrane in advance of deploying said stent, the deployment system including a respective deployment balloon for each of said membrane and said stent, and
 a common pressurizing system including a single inflation lumen for inflating and deflating the deployment balloons for said membrane and said stent.

2. The catheter of claim 1, wherein said deployment system is common to both said membrane and said stent.

3. The catheter of claim 1, wherein said deployment of the membrane in advance of the stent is controlled by differences in pressure-diameter characteristics of the respective deployment balloons.

4. The catheter of claim 1, wherein said deployable filter membrane is a selectively controllable collapsible mechanism.

5. An interventional device for alleviating a stenosed condition in a body lumen, said interventional device comprising:
 a catheter;
 a fixed guide wire located distally on and integral with said catheter;
 a stent delivery system with a stent located proximally of said fixed guide wire on said catheter, said stent delivery system including a first balloon configured to engage the stent;
 a debris collecting device mounted on said guide wire for collecting debris, said debris collecting device including a collapsible mechanism and a second balloon configured to engage the collapsible mechanism; and
 a common pressurization system including a single inflation lumen for inflating and deflating said first and second balloons.

6. The interventional device of claim 5, wherein said debris collecting device is arranged and adapted to be deployed automatically in advance of deployment of said stent during the same operation of said interventional device that results in deployment of said, stent.

7. The interventional device of claim 5, wherein said first and second balloons have different pressurization-diameter characteristics to enable automatic deployment of the debris collecting device in advance of deployment of the stent.

8. An interventional device for alleviating a stenosed condition in a body lumen, said interventional device comprising:
 a catheter;
 a fixed guide wire located distally on and integral with said catheter;
 a stent delivery system with a stent located proximally of said fixed guide wire on said catheter, said stent delivery system including a first balloon configured to engage the stent;
 a debris collecting device carried by said interventional device and arranged and adapted to be deployed automatically in advance of deployment of said stent for collecting debris, said debris collecting device including a collapsible mechanism and a second balloon configured to engage the collapsible mechanism; and
 a common pressurizing system including a single inflation lumen for inflating and deflating said first and second balloons.

9. The interventional device of claim 8, wherein said debris collecting device is arranged and adapted to be deployed automatically during the same operation of said interventional device that results in deployment of said stent.

10. The interventional device of claim 8, wherein said first and second balloons have different pressurization-diameter characteristics to enable automatic deployment of the debris collecting device in advance of deployment of the stent.

11. A stent delivery system, comprising:
 a catheter,
 a first balloon mounted on said catheter proximally of the distal end thereof, a stent firmly mounted on the first balloon, a fixed guide wire at a distal end of and integral with said catheter to facilitate advancement and exact placement of said stent in a vascular stenosis; and a protective device carried by said stent delivery system, said protective device being arranged and adapted to be deployed automatically in advance of deployment of said stent;

a second balloon coupled to the catheter configured to engage said protective device; and a common pressurizing system including a single inflation lumen for inflating and deflating said first and second balloons.

12. The stent delivery system of claim 11, wherein said protective device is arranged and adapted to be deployed automatically during the same operation of said stent delivery system that results in deployment of said stent.

13. A method of operating a balloon catheter stent delivery system, which comprises the steps of:

providing a balloon catheter stent delivery system for insertion into a stenosed lumen of a body vessel to alleviate the stenosis;

implementing a single inflation lumen of the balloon catheter delivery system to inflate a first balloon for deploying a fluid permeable membrane of the delivery system and also to inflate a second balloon for deploying the stent of the delivery system; and selecting the first and second balloons to have pressure-diameter characteristics such that the first balloon opens before the second balloon to deploy the fluid permeable membrane to capture debris while allowing perfusion of fluid therethrough in advance of deployment of the stent to compress the stenosed region of the lumen of the body vessel which may dislodge said debris.

* * * * *